United States Patent
Iwakura et al.

(10) Patent No.: US 9,534,060 B2
(45) Date of Patent: Jan. 3, 2017

(54) CARRIER FOR ANTIBODY PURIFICATION, MANUFACTURING METHOD FOR SAME, AND APPLICATION FOR SAME

(71) Applicant: DAISO CO., LTD., Osaka (JP)

(72) Inventors: Masahiro Iwakura, Tsukuba (JP); Kiyonori Hirota, Tsukuba (JP); Seiji Otaka, Osaka (JP)

(73) Assignee: Osaka Soda Co., Ltd., Osaka-shi (JP)

( * ) Notice: Subject to any disclaimer, the term of this patent is extended or adjusted under 35 U.S.C. 154(b) by 2 days.

(21) Appl. No.: 14/406,728

(22) PCT Filed: Jun. 11, 2013

(86) PCT No.: PCT/JP2013/066058
§ 371 (c)(1),
(2) Date: Dec. 9, 2014

(87) PCT Pub. No.: WO2013/187398
PCT Pub. Date: Dec. 19, 2013

(65) Prior Publication Data
US 2015/0152195 A1    Jun. 4, 2015

(30) Foreign Application Priority Data
Jun. 14, 2012    (JP) .................. 2012-134905

(51) Int. Cl.
| | | |
|---|---|---|
| C07K 17/14 | (2006.01) | |
| C07K 1/22 | (2006.01) | |
| C07K 14/31 | (2006.01) | |
| C07K 16/06 | (2006.01) | |
| B01D 15/38 | (2006.01) | |
| B01J 20/286 | (2006.01) | |
| B01J 20/32 | (2006.01) | |

(52) U.S. Cl.
CPC ........... *C07K 17/14* (2013.01); *B01D 15/3809* (2013.01); *B01J 20/286* (2013.01); *B01J 20/3204* (2013.01); *B01J 20/3217* (2013.01); *B01J 20/3274* (2013.01); *C07K 1/22* (2013.01); *C07K 14/31* (2013.01); *C07K 16/065* (2013.01); *C07K 2317/92* (2013.01)

(58) Field of Classification Search
None
See application file for complete search history.

(56) References Cited

U.S. PATENT DOCUMENTS

2009/0299035 A1    12/2009  Iwakura et al.

FOREIGN PATENT DOCUMENTS

| JP | 2990271 B1 | 12/1999 |
|---|---|---|
| JP | 3047020 B1 | 5/2000 |
| JP | 2005-112827 | 4/2005 |
| JP | 3740529 B2 | 2/2006 |
| JP | 4006523 B2 | 11/2007 |
| JP | 2008-115151 | 5/2008 |
| JP | 2008-115152 | 5/2008 |
| JP | 2008-115153 | 5/2008 |
| JP | 2008-266219 | 11/2008 |
| JP | 2008-266221 | 11/2008 |
| JP | 2009-156767 | 7/2009 |
| JP | 2010-127856 | 6/2010 |
| JP | 4528951 B2 | 8/2010 |
| JP | 2011-132140 | 7/2011 |
| JP | 2011-132141 | 7/2011 |
| JP | 2011-132145 | 7/2011 |

OTHER PUBLICATIONS

Hirota et al., "Kotai Iyakuhin no Tameno Tailor-Made Seisei Gijutsu Kaihatsu," *Chemical Engineering*, 56(4):293-299 (2011).
International Search Report and English Translation received in PCT Application No. PCT/JP2013/066058 dated Sep. 17, 2013.
English Translation of Written Opinion received in PCT Application No. PCT/JP2013/066058 dated Sep. 17, 2013.

*Primary Examiner* — Jacob Cheu
(74) *Attorney, Agent, or Firm* — Brinks Gilson & Lione (57) ABSTRACT

An object of the present invention is to provide a carrier on which Protein A has been immobilized, the Protein A having a specific amino acid sequence that permits the desorption of antibodies under mild pH conditions (specifically, pH 4.0 to 5.5) in which many antibodies do not undergo acid modification; and a manufacturing method for the carrier. An immobilization carrier (excluding an immobilization carrier having a monolith structure) on which a protein is adsorbed by electrostatic interaction, the protein consisting of an amino acid sequence represented by the general formula: R1-R2-R3-R4-R5-R6, wherein the part represented by R1-R2-R3 is used for immobilization on the immobilization carrier, wherein: the sequence represents a sequence from the amino-terminal side towards the carboxyl-terminal side; the sequence of the R2 part is the sequence of a Protein A mutant as a protein to be immobilized or a sequence in which 1 to 3 units of the sequence thereof were linked together, the Protein A mutant having characteristics of strongly binding to an antibody under neutral conditions and dissociating with the antibody bound under neutral conditions under weakly acidic conditions of pH 4.0 to 5.5.

16 Claims, 3 Drawing Sheets

CARRIER FOR ANTIBODY PURIFICATION, MANUFACTURING METHOD FOR SAME, AND APPLICATION FOR SAME

RELATED APPLICATIONS

This application is a 371 application of PCT/JP2013/066058 having an international filing date of Jun. 11, 2013, which claims priority to Japanese application No. 2012-134905 filed Jun. 14, 2012, the entire contents of which are incorporated herein by reference.

TECHNICAL FIELD

The present invention relates to a carrier for antibody purification and a manufacturing method for the same. The present invention further relates to an affinity chromatography column filled with a carrier for antibody purification, and a method for purifying an antibody using the column.

BACKGROUND ART

In recent years, the demand for an antibody drug having limited side effects, based on the antibody has been increasing yearly. Affinity chromatography using a carrier on which Protein A is immobilized is widely used as a means for purifying an antibody. Protein A as used here refers to *Staphylococcus aureus*-derived Protein A (described in A. Forsgren and J. Sjoquist, J. Immunol. (1966) 97, 822-827) or a portion of the domain sequences constituting the protein, capable of exhibiting the function of binding to an antibody.

A typical method for purifying an antibody using affinity chromatography using a carrier on which Protein A is immobilized is as follows. That is, the method involves (1) passing a raw material crude solution containing antibodies through a column filled with a carrier on which Protein A is immobilized to adsorb a desired antibody to the carrier, (2) washing the carrier to which the antibody is adsorbed with a neutral buffer solution to remove impurities, and then (3) eluting the antibody adsorbed to the carrier using an acidic buffer solution (specifically, pH 2.5 to 3.0).

The present inventors developed a technique involving introducing a Protein A-derived protein as a protein specifically binding to the Fc domain of an antibody while controlling orientation into an insoluble carrier by controlling orientation, as a means for efficiently purifying the antibody by increasing the capacity of binding to an antibody per carrier (see Patent Literatures 1 to 16).

The orientation-controlled immobilization method developed by the present inventors is as follows when expressed in a more generalized form.

The method is an orientation-controlled immobilization method comprising using a protein consisting of an amino acid sequence represented by the general formula: R1-R2-R3-R4-R5-R6, (wherein the sequence represents a sequence from the amino-terminal side towards the carboxyl-terminal side; the sequence of the R1 part may be absent, and, if present, is a sequence composed of amino acid residues other than lysine and cysteine residues; the sequence of the R2 part is a sequence of a Protein A-derived protein to be immobilized and a sequence adapted to comprise no lysine or cysteine residue so that it can hold a characteristic of binding to an antibody; the sequence of the R3 part may be absent, and, if present, is a spacer sequence composed of amino acid residues other than lysine and cysteine residues; the sequence of the R4 part is a sequence composed of 2 residues of amino acids represented by cysteine-X (wherein X represents lysine or an amino acid residue other than cysteine); the sequence of the R5 part may be absent, and, if present, is a sequence not comprising lysine or cysteine residues and a sequence comprising an acidic amino acid residue capable of rendering the isoelectric point of the whole protein consisting of an amino acid sequence represented by the general formula: R1-R2-R3-R4-R5-R6 on the acidic side; and the sequence of the R6 part is an affinity tag sequence for the purification of proteins) to cyanate the SH group of the sole existing cysteine residue in the R4 part, and reacting the cyanocysteinated protein with an insoluble carrier into which an amino group is introduced as a functional group to immobilize the part represented by R1-R2-R3 by the amide bonding between the carboxy terminus thereof and the amino group of the carrier.

Also in the purification of an antibody using the carrier immobilized by the orientation control of Protein A heretofore developed by the present inventors, a purification means has been applied which involves (1) passing a raw material crude solution containing antibodies through a column filled with a carrier on which Protein A is immobilized to adsorb a desired antibody to the carrier, (2) washing the carrier to which the antibody is adsorbed with a neutral buffer solution to remove impurities, and (3) eluting the antibody adsorbed to the carrier using an acidic buffer solution (specifically, pH 2.5 to 3.0), providing a means for efficiently purifying an antibody by the increased capacity of binding to an antibody per carrier.

However, the above method involving eluting an antibody using an acidic buffer solution having a pH of 2.5 to 3.0 has a serious flaw. Specifically, there is a problem that the contact of an antibody with a strongly acidic (e.g., pH 3.0 or less) buffer solution causes the acid modification of the antibody and changes the higher-order structure of the antibody, resulting in the induction of aggregation and the loss of the activity of the antibody as a medicine. The development of a more stable antibody molecule is attempted in order to solve the problem; however, it is obvious that such a solution cannot be a routine solution for a problem attending purification by affinity chromatography using a carrier on which Protein A is immobilized, and there is a need for the development of a method capable of being widely applied to the preparation of many antibody molecules.

CITATION LIST

Patent Literature

Patent Literature 1: JP Patent Publication (Kokai) No. 2011-132140 A
Patent Literature 2: JP Patent Publication (Kokai) No. 2011-132145 A
Patent Literature 3: JP Patent Publication (Kokai) No. 2011-132141 A
Patent Literature 4: JP Patent No. 2990271
Patent Literature 5: JP Patent No. 3047020
Patent Literature 6: JP Patent No. 3740529
Patent Literature 7: JP Patent Publication (Kokai) No. 2005-112827 A
Patent Literature 8: JP Patent No. 4528951
Patent Literature 9: JP Patent Publication (Kokai) No. 2008-115151 A
Patent Literature 10: JP Patent Publication (Kokai) No. 2008-115152 A
Patent Literature 11: JP Patent Publication (Kokai) No. 2008-115153 A Patent Literature 12: JP Patent Publication (Kokai) No. 2008-266219 A
Patent Literature 13: JP Patent Publication (Kokai) No. 2008-266221 A
Patent Literature 14: JP Patent Publication (Kokai) No. 2009-156767 A
Patent Literature 15: JP Patent Publication (Kokai) No. 2010-127856 A
Patent Literature 16: JP Patent No. 40006523

SUMMARY OF INVENTION

Technical Problem

To provide a routine solution for the above problem attending purification by affinity chromatography using a carrier on which a protein containing Protein A is immobilized, the present invention provides a carrier on which Protein A having a specific amino acid sequence permitting the desorption of antibodies under mild pH conditions (specifically, pH 4.0 to 5.5) in which many antibodies do not undergo acid modification is immobilized, and a manufacturing method therefor. In addition, it provides an affinity chromatography column for antibody purification, filled with a carrier on which a protein comprising Protein A is immobilized, and a method for purifying an antibody using the column.

Solution to Problem

The present inventors have carried out intensive studies for solving the above problem to be eliminated in the immobilization of Protein A.

The present inventors have obtained an idea that the above problem can be solved if a Protein A mutant can be developed as the Protein A used in the R2 part responsible for binding to antibodies among the sequence parts comprising an amino acid sequence represented by the general formula: R1-R2-R3-R4-R5-R6, utilized for the orientation-controlled immobilization of a protein, the Protein A mutant having a characteristic that in a step of passing an antibody-containing raw material crude solution through a column filled with a Protein A-immobilized carrier and adsorbing a desired antibody to the carrier followed by elution, during the purification of the antibody, it permits the desorption of the antibody in the range of pH 4.0 to 5.5 as mild pH conditions in eluting the antibody adsorbed to the carrier by using an acidic buffer solution, without affecting the operation of washing the carrier to which the antibody is adsorbed with a neutral buffer solution to remove impurities.

At a time point before accomplishing the present invention, the present inventors found that a Protein A exhibits a strong binding reaction to an antibody, the Protein A being adapted to contain no lysine or cysteine in the R2 part by substituting arginine or glycine for all lysine residues in the sequence derived from the A-domain of Protein A, represented by SEQ ID NO: 1 (JP Patent Publication (Kokai) Nos. 2011-132140 A, 2011-132145 A, and 2011-132141 A). Accordingly, a protein was prepared which consisted of a sequence adapted to the above general formula: R1-R2-R3-R4-R5-R6, containing the amino acid sequence of the Protein A (the protein is referred to as AD-1. SEQ ID NO: 2), and further exhaustive single amino acid substitutions were performed based on the sequence to prepare about 800 mutants of the AD-1. If a method for improving a protein as developed by the present inventors (JP Patent No. 4534030, Japanese Domestic Re-publication No 01/000797, M. Iwakura et al. J. Biol. Chem. 281, 13234-13246(2006), and JP Patent Publication (Kokai) No. 2005-058059 A) could be followed to determine the elution characteristic of an antibody under acidic conditions for all of the about 800 mutants, a mutant which is an object of the present invention was considered to be capable of being arrived at.

Sequence Derived from A-Domain of Protein A (SEQ ID NO: 1):

```
Ala-Asp-Asn-Asn-Phe-Asn-Lys-Glu-Gln-Gln

Asn-Ala-Phe-Tyr-Glu-Ile-Leu-Asn-Met-Pro

Asn-Leu-Asn-Glu-Glu-Gln-Arg-Asn-Gly-Phe

Ile-Gln-Ser-Leu-Lys-Asp-Asp-Pro-Ser-Gln

Ser-Ala-Asn-Leu-Leu-Ser-Glu-Ala-Lys-Lys

Leu-Asn-Glu-Ser-Gln-Ala-Pro-Lys
```

Sequence of AD-1 (Sequence Prepared by Adaptation to Form of R1-R2-R3-R4-R5-R6 Based on A-Domain Sequence of Protein A) (SEQ ID NO: 2):

```
Ala-Asp-Asn-Asn-Phe-Asn-Arg-Glu-Gln-Gln

Asn-Ala-Phe-Tyr-Glu-Ile-Leu-Asn-Met-Pro

Asn-Leu-Asn-Glu-Glu-Gln-Arg-Asn-Gly-Phe

Ile-Gln-Ser-Leu-Arg-Asp-Asp-Pro-Ser-Gln

Ser-Ala-Asn-Leu-Leu-Ser-Glu-Ala-Arg-Arg

Leu-Asn-Glu-Ser-Gln-Ala-Pro-Gly-Gly-Gly

Gly-Gly-Cys-Ala-Asp-Asp-Asp-Asp-Asp-Asp

His-His-His-His-His-His
```

Here, R1, R2, R3, R4, R5, and R6 of the sequence (AD-1) shown in SEQ ID NO: 2 in the general formula: R1-R2-R3-R4-R5-R6 are the following sequences.

R1 (methionine derived from the start codon for expression in *Escherichia coli*, typically absent because of being almost removed with expression):
Met R2 (a sequence in which the amino acid sequence of the A-domain of Protein A is modified to contain no cysteine and lysine) (SEQ ID NO: 3):

```
Ala-Asp-Asn-Asn-Phe-Asn-Arg-Glu-Gln-Gln

Asn-Ala-Phe-Tyr-Glu-Ile-Leu-Asn-Met-Pro

Asn-Leu-Asn-Glu-Glu-Gln-Arg-Asn-Gly-Phe

Ile-Gln-Ser-Leu-Arg-Asp-Asp-Pro-Ser-Gln

Ser-Ala-Asn-Leu-Leu-Ser-Glu-Ala-Arg-Arg

Leu-Asn-Glu-Ser-Gln-Ala-Pro-Gly
```

R3 (a linker sequence containing no cysteine and lysine):
Gly-Gly-Gly-Gly

R4 (a sequence for causing immobilization reaction via cyanocysteine):
Cys-Ala

R5 (a sequence for rendering the isoelectric point negative):
Asp-Asp-Asp-Asp-Asp-Asp R6 (a tag sequence for purification):
His-His-His-His-His-His The present inventors exhaustively prepared mutant proteins in which all of the amino acid residues constituting R2 were subjected to single amino acid substitution based on the amino acid sequence named AD-1.

However, it was difficult, in view of previous findings, to efficiently select a mutant protein having a specific amino acid sequence permitting the desorption of antibodies under mild pH conditions (pH 4.0 to 5.5) in which many antibodies did not undergo acid modification, which was an object of the present invention from among as many as 800 single amino acid substitution mutants. Thus, the purpose of obtaining the above mutant protein could not be achieved. This is because to determine whether a mutant had a desired characteristic or not, it was necessary to immobilize all of candidate mutants on the carrier, prepare an affinity column, and perform a purification experiment using the prepared column Thus, only determining a desired characteristic for one mutant takes several days to 2 weeks; it was practically difficult from the viewpoint of time and cost to apply the operation to the about 800 single amino acid substitutions.

As a result of intensive studies under such circumstances, the present inventors have conceived the use of an array analysis apparatus as already developed by the present inventors (JP Patent No. 4528951, JP Patent Publication (Kokai) No. 2010-127856 A, and JP Patent No. 4006523).

In an array analysis apparatus used in the present invention, an array substrate uses a thin layer of silica monolith porous material as a supporting layer. Poly-L-lysine is introduced into the surface of the silica monolith porous material, and a mutant is spotted on the thin layer using a spotter to adsorb the mutant protein thereto by ionic interaction, followed by cyanating the SH group of a cysteine residue in the protein adsorbed on the spot using a cyanation reagent for an orientation-controlled immobilization reaction via the cyanocysteine. Thereafter, the resultant has been washed with a buffer solution having a high salt concentration to remove the R4-R5-R6-derived part in the mutant protein, and an array substrate on which the R1-R2-R3 part has been immobilized to form spots in an orientation-controlled form on the silica monolith porous material at the carboxy terminus thereof. The array substrate on which the mutant protein was immobilized has been (1) subjected to the passage of an antibody solution, (2) washed with a neutral buffer solution, (3) subjected to the passage of a pH 5.0 buffer solution as a buffer solution for antibody elution, and then (4) subjected to the passage of a pH 2.5 buffer solution for regeneration. During the process, a change in the volume of transmitted light at 280 nm in each spot has been measured with time by using the array analysis apparatus. When the antibody binds to each mutant spot, the volume of transmitted light at 280 nm is decreased with absorption at 280 nm by the bound antibody.

When the antibody is dissociated from each mutant spot with the elution of the antibody, the volume of transmitted light at 280 nm is increased. In this measurement, the logarithm of the volume of transmitted light at 280 nm (a volume corresponding to the amount of change in absorbance) when the pH 5.0 buffer solution was passed as a buffer solution for antibody elution (the above step (3)) was taken, and plotted against the elapsed time. The elapsed time ($T_{0.5}$) has been determined until the difference is reduced by half between the value of the logarithm of the volume of transmitted light at 280 nm when the pH 5.0 buffer solution is passed and the value of the logarithm of the volume of transmitted light at 280 nm after the passage of the pH 2.5 buffer solution for regeneration (the above step (4)). Using the value of the time as an indication, mutants giving as small a value as possible have been selected out. Then, mutants in each of which mutations giving small $T_{0.5}$ are combined have been prepared and similarly measured, and combination mutants have been prepared and measured for the value of $T_{0.5}$. A desired mutant has been able to be found among such combination mutants. A mutant in which some repeats of the found mutant sequence are linked has been prepared, and a carrier subjected to the orientation-controlled immobilization thereof has been prepared. An affinity column has been prepared using this carrier; elution has been performed under elution conditions of various pH values; and the chromatogram has been analyzed. As a result, it has been confirmed that the object of the present invention of obtaining a carrier containing a Protein A having a specific amino acid sequence permitting the desorption of an antibody under mild pH conditions has been achieved, thereby accomplishing the present invention.

Thus, the present invention is as follows.

[1] An immobilization carrier, excluding an immobilization carrier having a monolith structure, on which a protein is adsorbed by electrostatic interaction, the protein consisting of an amino acid sequence represented by the general formula: R1-R2-R3-R4-R5-R6, wherein the part represented by R1-R2-R3 is used for immobilization on the immobilization carrier, wherein:

the sequence represents a sequence from the amino-terminal side towards the carboxyl-terminal side;

the sequence of the R1 part may be absent, and, if present, is a sequence composed of amino acid residues other than lysine and cysteine residues;

the sequence of the R2 part is the sequence of a Protein A mutant as a protein to be immobilized or a sequence in which 1 to 3 units of the sequence thereof were linked together and is a sequence not comprising a lysine or cysteine residue, the Protein A mutant having characteristics of strongly binding to an antibody under neutral conditions and dissociating with the antibody bound under neutral conditions under weakly acidic conditions of pH 4.0 to 5.5;

the sequence of the R3 part may be absent, and, if present, is a spacer sequence composed of amino acid residues other than lysine and cysteine residues;

the sequence of the R4 part is a sequence composed of 2 residues of amino acids represented by cysteine-X wherein X represents alanine or an amino acid residue other than alanine and cysteine;

the sequence of the R5 part may be absent, and, if present, is a sequence not comprising a lysine and cysteine residues and a sequence comprising an acidic amino acid residue capable of rendering the isoelectric point of the whole protein consisting of an amino acid sequence represented by the general formula: R1-R2-R3-R4-R5-R6 on the acidic side; and the sequence of the R6 part is an affinity tag sequence for the purification of proteins.

[2] The immobilization carrier according to [1], wherein the Protein A mutant is a Protein A mutant the elapsed time of which until the half amount of the bound antibody is dissociated ($T_{0.5}$) when an antibody is bound to the Protein A mutant immobilized on an array substrate and eluted with a 0.1 M sodium citrate solution of pH 5.0, and the dissociation constant thereof with the antibody are reduced compared to the $T_{0.5}$ and dissociation constant for the Protein A mutant represented by SEQ ID NO: 3.

[3] The immobilization carrier according to [1] or [2], wherein the Protein A mutant is a mutant consisting of an amino acid sequence in which 1 to 3 amino acid residues are substituted in the amino acid sequence of a Protein A derived from *Staphylococcus aureus*.

[4] The immobilization carrier according to any one of [1] to [3], wherein the Protein A mutant is a mutant of the A-domain of Protein A.

[5] The immobilization carrier according to any one of [1] to [4], wherein the sequence of the R2 part is the sequence of a mutant protein of the A-domain of a Protein A consisting of any sequence of SEQ ID NOS: 4 to 7 or a sequence in which 1 to 3 units of the sequence of a mutant protein of the A-domain of a Protein A consisting of any sequence of SEQ ID NOS: 4 to 7 are linked together.

[6] The immobilization carrier according to any one of [1] to [5], for converting the sulfhydryl group of the sole cysteine residue present in a protein consisting of an amino acid sequence represented by the general formula: R1-R2-R3-R4-R5-R6 to a thiocyano group and causing the resultant to act on any immobilization carrier having a primary amine as a functional group for binding the R1-R2-R3 part which is the amino acid sequence part present amino-terminal side to the cysteine residue of the protein to the carrier by amide bonding.

[7] The immobilization carrier according to any one of [1] to [6], wherein the sequence of the R3 part in an amino acid sequence represented by the general formula: R1-R2-R3-R4-R5-R6 is a sequence consisting of 1 to 10 glycine residues.

[8] The immobilization carrier according to any one of [1] to [7], wherein the sequence of the R5 part in an amino acid sequence represented by the general formula: R1-R2-R3-R4-R5-R6 is a sequence of 1 to 10 amino acid residues consisting of amino acid residues of aspartic acid and/or glutamic acid.

[9] The immobilization carrier according to any one of [1] to [8], wherein the sequence of the R5 part in an amino acid sequence represented by the general formula: R1-R2-R3-R4-R5-R6 is a sequence consisting of 1 to 10 aspartic acid residues.

[10] The immobilization carrier according to any one of [1] to [9], wherein the sequence of the R6 part in an amino acid sequence represented by the general formula: R1-R2-R3-R4-R5-R6 is a sequence consisting of 4 or more histidine residues.

[11] The immobilization carrier according to any one of [1] to [10], wherein the carrier is selected from the group consisting of silica carriers, glass beads, and polymers.

[12] A method for preparing the immobilization carrier according to any one of [1] to [11], comprising adsorbing a protein consisting of an amino acid sequence represented by the general formula: R1-R2-R3-R4-R5-R6 to a carrier by electrostatic interaction.

[13] An immobilization carrier on which a Protein A mutant is immobilized, produced by converting the sulfhydryl group of the sole cysteine residue present in the protein consisting of an amino acid sequence represented by the general formula: R1-R2-R3-R4-R5-R6 according to any one of [1] to [11] to a thiocyano group and causing the resultant to act on any immobilization carrier having a primary amine as a functional group for binding the R1-R2-R3 part as an amino acid sequence part present amino-terminal side to the cysteine residue of the protein to the carrier by amide bonding.

[14] A method for preparing the immobilization carrier according to [12], comprising converting the sulfhydryl group of the sole cysteine residue present in the protein consisting of an amino acid sequence represented by the general formula: R1-R2-R3-R4-R5-R6 according to any one of [1] to [11] to a thiocyano group and causing the resultant to act on any immobilization carrier having a primary amine as a functional group for binding the R1-R2-R3 part as an amino acid sequence part present amino-terminal side to the cysteine residue of the protein to the carrier by amide bonding.

[15] An affinity chromatography column for antibody purification, filled with the immobilization carrier according to [13].

[16] A method for purifying an antibody, comprising applying a solution comprising an antibody to the affinity chromatography column for antibody purification according to [15] to bind the antibody to the Protein A mutant and then dissociating and eluting the antibody using an elution buffer solution.

[17] A method for designing a protein consisting of an amino acid sequence represented by the general formula: R1-R2-R3-R4-R5-R6 used for immobilization of a protein consisting of an amino acid sequence represented by R1-R2-R3 on an immobilization carrier, comprising selecting the amino acid sequences of the R1, R2, R3, R4, R5, and R6 parts so as to conform to the following conditions:

(a) permitting the sequence of the R1 part to be absent, or, if permitting the presence thereof, selecting a sequence composed of amino acid residues other than lysine and cysteine residues;

(b) as the sequence of the R2 part, selecting the sequence of a Protein A mutant or a sequence in which 1 to 3 units of the sequence thereof are linked together and is a sequence not comprising a lysine or cysteine residue, the Protein A mutant having characteristics of strongly binding to an antibody under neutral conditions and dissociating with the antibody bound under neutral conditions under weakly acidic conditions of pH 4.0 to 5.5;

(c) permitting the sequence of the R3 part to be absent, or, if permitting the presence thereof, selecting a spacer sequence composed of amino acid residues other than lysine and cysteine residues;

(d) as the sequence of the R4 part, selecting a sequence composed of 2 residues of amino acids represented by cysteine-X (wherein X represents alanine or an amino acid residue other than cysteine);

(e) permitting the sequence of the R5 part to be absent, or, if permitting the presence thereof, selecting a sequence not comprising a lysine or cysteine residue, wherein the sequence comprises an acidic amino acid residue capable of rendering the isoelectric point of the whole protein consisting of an amino acid sequence represented by the general formula: R1-R2-R3-R4-R5-R6 on the acidic side; and (f) as the sequence of the R6 part, selecting an affinity tag sequence for purifying a protein.

[18] The method according to [17], wherein the Protein A mutant is a Protein A mutant the elapsed time of which until the half amount of the bound antibody is dissociated ($T_{0.5}$) when an antibody is bound to the Protein A mutant immobilized on an array substrate and eluted with a 0.1 M sodium citrate solution of pH 5.0, and the dissociation constant thereof with the antibody are reduced compared to $T_{0.5}$ and the dissociation constant for the Protein A mutant represented by SEQ ID NO: 3.

[19] The method according to [17] or [18], wherein the Protein A mutant is a mutant consisting of an amino acid sequence in which 1 to 3 amino acid residues are substituted in the amino acid sequence of Protein A derived from *Staphylococcus aureus*.

[20] The method according to any one of [17] to [19], wherein the Protein A mutant is a mutant of the A-domain of Protein A.

[21] The method according to any one of [17] to [20], wherein the sequence of the R2 part is the sequence of a mutant protein of the A-domain of a Protein A consisting of any sequence of SEQ ID NOS: 4 to 7 or the sequence of a mutant protein of the A-domain of Protein A consisting of a sequence in which 1 to 3 units of any sequence of SEQ ID NOS: 4 to 7 are linked together.

The present specification encompasses the contents of the specification and/or drawings of Japanese Patent Application No. 2012-134905 on which the priority of the present application is based.

Advantageous Effects of Invention

According to the method of the present invention, an immobilization carrier excellent in elution performance can be obtained, which permits the elution of a Protein A-bound antibody under milder pH conditions (pH 4.0 to 5.5) in purifying the antibody by designing an amino acid sequence represented by the general formula: R1-R2-R3-R4-R5-R6 containing a Protein A mutant as R2, preparing a protein consisting of the amino acid sequence, and immobilizing the Protein A mutant on a carrier using the protein. The use of the immobilization carrier permits the elution of an antibody under mild pH conditions (pH 4.0 to 5.5) and improves the recovery rate of the antibody obtained. In addition, the use of the immobilization carrier as a filler can provide an affinity chromatography column excellent in purifying capability, and an efficient method for purifying an antibody can also be provided using the column.

DESCRIPTION OF EMBODIMENTS

The present invention will be described below in detail.

The sequence of the R2 part in a protein consisting of an amino acid sequence represented by the general formula: R1-R2-R3-R4-R5-R6 according to the present invention is a Protein A to be immobilized, and the use of the protein consisting of an amino acid sequence represented by the general formula: R1-R2-R3-R4-R5-R6 can provide an immobilized protein in which the R2 part is immobilized. In the above general formula, the sequence represents an amino acid sequence from the amino-terminal side towards the carboxyl-terminal side.

The sequence of the R1 part may be absent, and, if present, is a sequence composed of amino acid residues other than lysine and cysteine residues. Specific examples thereof include methionine derived from the start codon for expression in *Escherichia coli*. However, the methionine is typically absent because of being almost removed with expression.

The sequence of the R2 part is the amino acid sequence of a mutant of the naturally occurring Protein A consisting of the amino acid sequence represented by SEQ ID NO: 1. An amino acid sequence using the amino acid sequence of a mutant of Protein A as a sequence unit and consisting of repeats of the sequence unit may be used. In this case, the number of repeats is 1 to 3. Here, the amino acid sequence consisting of the repeats is also referred to as a sequence in which 1 to 3 units of the amino acid sequence of a mutant of Protein A are linked together. The amino acid sequence of the mutant of Protein A used in the R2 part contains no lysine residue and cysteine residue. The mutant of Protein A used has characteristics of strongly binding to an antibody under neutral conditions and dissociating with the antibody bound under neutral conditions under weakly acidic conditions of pH 4.0 to 5.5.

As an example of a Protein A as the R2 part, a Protein A mutant can be listed which is obtained by modifying the amino acid sequence of Protein A derived from *Staphylococcus aureus* (described in A. Forsgren and J. Sjoquist, J. Immunol. (1966) 97, 822-827) by design using a common genetic modification technique. The protein as the R2 part may be a mutant of the domain of Protein A capable of binding to the Fc region of an antibody. Examples of the domain include the E-domain, D-domain, A-domain, B-domain, and C-domain. Among these, a mutant of the A-domain is preferable. For the purpose of the present invention, the term "Protein A" also includes these domains.

When a lysine residue, having an ε-amino group, or a cysteine residue, having a sulfhydryl group, is contained in the amino acid sequence of Protein A, lysine and cysteine are substituted with other amino acids so that the activity of the Protein A binding to an antibody is not reduced, to ensure no containment of lysine and cysteine in the amino acid sequence of the Protein A. The present inventors already established a method for preparing a protein containing no lysine or cysteine (JP Patent Publication (Kokai) No. 2008-266219 A). Based on the amino acid sequence of naturally occurring Protein A, the amino acid sequence can be modified according to the method to prepare a Protein A consisting of an amino acid sequence composed of 18 amino acids including no lysine or cysteine residues, which is a protein capable of exhibiting performance comparable to that of the naturally occurring Protein A in the characteristic binding to an antibody.

The amino acid sequence of the A-domain of Protein A derived from *Staphylococcus aureus* is shown in SEQ ID NO: 1.

Sequence derived from A-domain of Protein A (SEQ ID NO: 1):

```
Ala-Asp-Asn-Asn-Phe-Asn-Lys-Glu-Gln-Gln

Asn-Ala-Phe-Tyr-Glu-Ile-Leu-Asn-Met-Pro

Asn-Leu-Asn-Glu-Glu-Gln-Arg-Asn-Gly-Phe

Ile-Gln-Ser-Leu-Lys-Asp-Asp-Pro-Ser-Gln

Ser-Ala-Asn-Leu-Leu-Ser-Glu-Ala-Lys-Lys

Leu-Asn-Glu-Ser-Gln-Ala-Pro-Lys
```

The Protein A has 4 lysine residues (at the 35th, 49th, 50th and 58th amino acid positions), and the amino acid sequence of the A-domain of Protein A in which the lysine residues are substituted by arginine residues or a glycine residue is shown in SEQ ID NO: 3 below.

Sequence in which A-domain of Protein A is modified to contain no cysteine and lysine (SEQ ID NO: 3):

```
Ala-Asp-Asn-Asn-Phe-Asn-Arg-Glu-Gln-Gln

Asn-Ala-Phe-Tyr-Glu-Ile-Leu-Asn-Met-Pro

Asn-Leu-Asn-Glu-Glu-Gln-Arg-Asn-Gly-Phe

Ile-Gln-Ser-Leu-Arg-Asp-Asp-Pro-Ser-Gln

Ser-Ala-Asn-Leu-Leu-Ser-Glu-Ala-Arg-Arg

Leu-Asn-Glu-Ser-Gln-Ala-Pro-Gly
```

Examples of the A-domain of Protein A having characteristics of strongly binding to an antibody under neutral conditions and dissociating with the antibody bound under neutral conditions under weakly acidic conditions of pH 4.0 to 5.5, modified based on the amino acid sequence shown in SEQ ID NO: 3 include the following mutants. A protein consisting of an amino acid sequence represented by the general formula: R1-R2-R3-R4-R5-R6, containing the amino acid sequence of each mutant as the R2 part is called AD-3, AD-4, AD-6-1, and AD-6-2.

The mutant of the A-domain of Protein A as the R2 part of AD-3 consists of the following amino acid sequence (SEQ ID NO: 4), in which E (glutamic acid) at the 15th position and G (glycine) at the 29th position are substituted by H (histidine) and A (alanine), respectively in the amino acid sequence of SEQ ID NO: 3.

Amino acid sequence of AD-3 (SEQ ID NO: 4):

```
Ala-Asp-Asn-Asn-Phe-Asn-Arg-Glu-Gln-Gln

Asn-Ala-Phe-Tyr-His-Ile-Leu-Asn-Met-Pro

Asn-Leu-Asn-Glu-Glu-Gln-Arg-Asn-Ala-Phe

Ile-Gln-Ser-Leu-Arg-Asp-Asp-Pro-Ser-Gln

Ser-Ala-Asn-Leu-Leu-Ser-Glu-Ala-Arg-Arg

Leu-Asn-Glu-Ser-Gln-Ala-Pro-Gly
```

The mutant of the A-domain of Protein A as the R2 part of AD-4 consists of the following amino acid sequence (SEQ ID NO: 5), in which E (glutamic acid) at the 15th position, M (methionine) at the 19th position, and G (glycine) at the 29th position are substituted by H (histidine), V (valine), and A (alanine), respectively in the amino acid sequence of SEQ ID NO: 3.

Amino acid sequence of AD-4 (SEQ ID NO: 5):

```
Ala-Asp-Asn-Asn-Phe-Asn-Arg-Glu-Gln-Gln

Asn-Ala-Phe-Tyr-His-Ile-Leu-Asn-Val-Pro

Asn-Leu-Asn-Glu-Glu-Gln-Arg-Asn-Ala-Phe

Ile-Gln-Ser-Leu-Arg-Asp-Asp-Pro-Ser-Gln

Ser-Ala-Asn-Leu-Leu-Ser-Glu-Ala-Arg-Arg

Leu-Asn-Glu-Ser-Gln-Ala-Pro-Gly
```

The mutant of the A-domain of Protein A as the R2 part of AD-6-1 consists of the following amino acid sequence (SEQ ID NO: 6), in which E (glutamic acid) at the 15th position, M (methionine) at the 19th position, and G (glycine) at the 29th position are substituted by H (histidine), V (valine), and E (glutamic acid), respectively in the amino acid sequence of SEQ ID NO: 3.

Amino acid sequence of AD-6-1 (SEQ ID NO: 6):

```
Ala-Asp-Asn-Asn-Phe-Asn-Arg-Glu-Gln-Gln

Asn-Ala-Phe-Tyr-His-Ile-Leu-Asn-Val-Pro

Asn-Leu-Asn-Glu-Glu-Gln-Arg-Asn-Glu-Phe

Ile-Gln-Ser-Leu-Arg-Asp-Asp-Pro-Ser-Gln

Ser-Ala-Asn-Leu-Leu-Ser-Glu-Ala-Arg-Arg

Leu-Asn-Glu-Ser-Gln-Ala-Pro-Gly
```

The mutant of the A-domain of Protein A as the R2 part of AD-6-2 consists of the following amino acid sequence (SEQ ID NO: 7), in which E (glutamic acid) at the 15th position, M (methionine) at the 19th position, and G (glycine) at the 29th position are substituted by H (histidine), V (valine), and D (aspartic acid), respectively in the amino acid sequence of SEQ ID NO: 3.

Amino acid sequence of AD-6-2 (SEQ ID NO: 7):

```
Ala-Asp-Asn-Asn-Phe-Asn-Arg-Glu-Gln-Gln

Asn-Ala-Phe-Tyr-His-Ile-Leu-Asn-Val-Pro

Asn-Leu-Asn-Glu-Glu-Gln-Arg-Asn-Asp-Phe

Ile-Gln-Ser-Leu-Arg-Asp-Asp-Pro-Ser-Gln

Ser-Ala-Asn-Leu-Leu-Ser-Glu-Ala-Arg-Arg

Leu-Asn-Glu-Ser-Gln-Ala-Pro-Gly
```

The sequence of the R3 part is any spacer sequence composed of amino acid residues other than lysine and cysteine residues. The R3 part may be absent. The sequence of the R3 part is immobilized together with the R2 part on an immobilization carrier. The R3 part assumes a role as a suitable linker for preventing the inhibition of the function of the R2 part by the binding thereof to the immobilization carrier in immobilization. The role as a linker is to keep a suitable distance between a protein having a specific function as the R2 part and the immobilization carrier. Thus, the R3 part is required to be any amino acid sequence having a constant length and inactive. The number of amino acids in the R3 part is not limited; however, it is 0 (i.e., absent), or 1 to 10, preferably 2 to 5. Examples of the sequence of the R3 part include a polyglycine consisting of 0 to 10 or 2 to 5 glycine residues; specific examples thereof include the sequence represented by Gly-Gly-Gly-Gly.

The sequence of the R4 part is a sequence composed of 2 amino acid residues represented by cysteine-X (X: an amino acid residue other than lysine and cysteine); examples thereof include Cys-Ala. In a protein consisting of an amino acid sequence represented by the general formula: R1-R2-R3-R4-R5-R6, only the R4 sequence part has the sole cysteine residue. Thus, the SH group of the sole cysteine residue as a side-chain functional group thereof can be cyanated to convert the residue to a cyanocysteine residue, followed by reacting the cyanocysteine residue with a primary amine on the immobilization carrier to immobilize only the part represented by R1-R2-R3 of an amino acid sequence represented by the general formula: R1-R2-R3-R4-R5-R6 on the immobilization carrier by orientation control.

The sequence of the R5 part is any sequence comprising no lysine residue and cysteine residue and a sequence comprising an acidic amino acid residue capable of rendering the isoelectric point of the whole amino acid sequence represented by the general formula: R1-R2-R3-R4-R5-R6 on the acidic side. As used herein, the "sequence comprising an acidic amino acid residue capable of rendering the isoelectric point of the whole protein on the acidic side" refers to a sequence containing types and a number of acidic amino acid residues enough to be capable of rendering the isoelectric point of the whole protein on the acidic side. The R5 part is preferably a sequence enriched in aspartic acid and glutamic acid. The isoelectric point of a protein depends on the type and number of constituent amino acid residues. For example, enrichment in basic amino acids such as lysine and arginine requires a number of aspartic acid or glutamic acid exceeding the total number of the basic amino acids. One of ordinary skill in the art can easily estimate the isoelectric point of a protein by calculation. The sequence enriched in aspartic acid or glutamic acid may be designed so that the isoelectric point of the protein consisting of an amino acid sequence represented by the general formula: R1-R2-R3-R4-R5-R6 is a value between 4 and 5. The number of amino acids in the sequence of the R5 part is not limited; however, it is 0 (i.e., absent), or 1 to 20, preferably 1 to 10, or 0 to 20, preferably 0 to 10. Examples thereof include a polyaspartic acid consisting of 2 to 10 aspartic acid residues. When the isoelectric point of the part containing no R5 part is acidic from the beginning, the R5 part may be absent.

The sequence of the R6 part is any affinity tag sequence capable of binding to a specific compound. The sequence of the R6 part is a sequence part used for purifying a synthesized protein consisting of an amino acid sequence represented by the general formula: R1-R2-R3-R4-R5-R6. Examples of the sequence of the R6 part include a sequence capable of binding to a specific compound, i.e., an affinity tag sequence. When a protein containing the tag is purified using an antibody specific for the tag, it is sometimes referred to as an epitope tag. Examples of the affinity tag sequence include a polyhistidine sequence consisting of 2 to 12, preferably 4 or more, more preferably 4 to 7, still more preferably 5 or 6 histidine residues; specific examples thereof include His-His-His-His-His-His. In this case, nickel chelate column chromatography using nickel as a ligand can be utilized to purify the above polypeptide. The purification can also be performed by affinity chromatography using a column on which an antibody to the polyhistidine is immobilized as a ligand. In addition, a HAT tag, a HN tag, or the like consisting of a sequence containing histidine can also be used.

A specific example of a protein for immobilization consisting of an amino acid sequence represented by the general formula: R1-R2-R3-R4-R5-R6 is shown in SEQ ID NO: 2.

Sequence of AD-1 (Sequence Prepared by Adaptation to Form of R1-R2-R3-R4-R5-R6 Based on A-Domain Sequence of Protein A) (SEQ ID NO: 2):

Ala-Asp-Asn-Asn-Phe-Asn-Arg-Glu-Gln-Gln

Asn-Ala-Phe-Tyr-Glu-Ile-Leu-Asn-Met-Pro

-continued

Asn-Leu-Asn-Glu-Glu-Gln-Arg-Asn-Gly-Phe

Ile-Gln-Ser-Leu-Arg-Asp-Asp-Pro-Ser-Gln

Ser-Ala-Asn-Leu-Leu-Ser-Glu-Ala-Arg-Arg

Leu-Asn-Glu-Ser-Gln-Ala-Pro-Gly-Gly-Gly

Gly-Gly-Cys-Ala-Asp-Asp-Asp-Asp-Asp-Asp

His-His-His-His-His-His

In the sequence shown in SEQ ID NO: 2, the R1 part is absent; the R2 part is the amino acid sequence of the A-domain of Protein A containing no lysine or cysteine (SEQ ID NO: 3); the R3 part is the sequence represented by Gly-Gly-Gly-Gly; the R4 part is the sequence represented by Cys-Ala; the R5 part is the sequence represented by Asp-Asp-Asp-Asp-Asp-Asp; and the R6 part is the sequence represented by His-His-His-His-His-His.

The R1 part, R3 part, R4 part, R5 part, and R6 part of AD-3, AD-4, AD-6-1, and AD-6-2 are the same as those of AD-1.

The immobilization of a protein to be immobilized using a protein for immobilization consisting of an amino acid sequence represented by the general formula: R1-R2-R3-R4-R5-R6 according to the present invention on a carrier can be carried out according to a method as described in JP Patent No. 3788828, 2990271, or 3047020 or JP Patent Publication (Kokai) No. 2003-344396 A, 2008-115151 A, 2008-115152 A, 2008-115153 A, or 2008-266221 A, or the like.

Specifically, the cysteine residue in the R4 part of a protein consisting of an amino acid sequence represented by the general formula: R1-R2-R3-R4-R5-R6 according to the present invention is cyanated to make a cyanocysteine residue, followed by reacting the cyanocysteine-containing protein with an immobilization carrier having a primary amino group represented by the general formula "NH$_2$—Y" (where Y represents any immobilization carrier) as a functional group under weakly alkaline conditions (pH 8 to 10) to immobilize the R1-R2-R3 part on the immobilization carrier. The R1-R2-R3 part bound to the immobilization carrier is represented by R1-R2-R3-CO—NH—Y (where Y has the above meaning), and the R1-R2-R3 part binds at one carboxy terminus in the R2 part to the immobilization carrier. The cyanation reaction can be performed using a cyanation reagent. The cyanation reagent may be 2-nitro-5-thiocyanobennzoic acid (NTCB) (see Y. Degani, A. Ptchornik, Biochemistry, 13, 1-11 (1974)), 1-cyano-4-dimethylaminopyridinium tetrafluoroborate (CDAP), or the like.

In the method described in JP Patent Publication (Kokai) No. 2003-344396 A, a protein consisting of an amino acid sequence corresponding to the amino acid sequence represented by the general formula: R1-R2-R3-R4-R5-R6 according to the present invention is adsorbed to an immobilization carrier, followed by cyanating the cysteine residue and then performing the above reaction to immobilize a protein consisting of an amino acid sequence represented by R1-R2-R3 on the immobilization carrier. To adsorb the protein to the immobilization carrier, the protein may be reacted with the immobilization carrier under neutral to weakly alkaline conditions (pH 7 to 10). Under weakly alkaline conditions, the protein is negatively charged, while the immobilization carrier is positively charged; they adsorb and bind to each other by electrostatic interaction.

The present invention is an immobilization carrier on which is adsorbed a protein consisting of an amino acid sequence represented by the general formula: R1-R2-R3-R4-R5-R6, and encompasses an immobilization carrier before cyanating the cysteine residue and an immobilization carrier on which is immobilized the part represented by R1-R2-R3 by cyanation.

Many unreacted primary amines are present in the immobilization carrier part in the immobilized protein in which the R1-R2-R3 part is immobilized, prepared by immobilization reaction via cyanocysteine using a protein consisting of an amino acid sequence represented by the general formula: R1-R2-R3-R4-R5-R6 according to the present invention. When a lysine residue or a cysteine residue is present in the immobilized protein, it is likely that the remaining activated amines restrict the utilization of the immobilized protein of the present invention. However, because the R1-R2-R3 part as the immobilized protein part contains no lysine residue and cysteine residue, the primary amines remaining on the carrier surface on which the protein is immobilized can be treated with a masking agent without changing the chemical control of the protein part. The masking agent is preferably acetic anhydride, maleic anhydride, or the like; however, any masking agent can be used.

The present invention further provides an immobilized protein in which the protein consisting of an amino acid sequence containing no cysteine residue and lysine residue obtained by the above method is firmly bound to an immobilization carrier having primary amino groups via a linker sequence by amide (peptide) bonding.

In the present invention, a carrier capable of being used for chromatography can be used as a carrier for immobilization. However, the carrier used in the present invention does not include a carrier having a monolith structure. Here, the monolith structure is a porous body having macropores extending therethrough from the upper face to the lower face; the porous body is characterized by having micropores inside the macropores; and the porous body has macropores of 1 to 100 μm and micropores of 0 to 100 nm. Examples of the monolith structure include a silica monolith structure containing silicon. The monolith structure is described in JP Patent Publication (Kokoku) No. 8-029952 B, JP Patent Publication (Kokai) Nos. 07-041374 A and 2010-127853 A, and the like.

The immobilization carrier includes any insoluble carrier on which a protein can be immobilized, such as a particulate carrier, a film-form carrier, a fibrous carrier, a holofiber-form carrier, a plate-like or sheet-like substrate, and a magnetic bead. The "immobilization carrier" includes an "immobilization substrate". The materials forming carriers having such shapes may each be any material into the surface of which functional groups for the orientation-controlled immobilization of a mediated protein are introduced; a wide variety of materials can be used, including a polymer material as a polymer or copolymer typified by polyethylene, polypropylene, polystyrene, polystyrene divinylbenzene, polymethacrylate, polyvinyl alcohol, polyester, or polyacrylate, a natural material typified by hydrogel, agarose, dextran, cellulose, chitosan, or the like, an inorganic material typified by silica, glass, ceramic, or the like, and further a metal material typified by gold, alumina, silver, or the like. The carrier may be a commercially available carrier such as Sepharose®, Sephadex®, or Cellufine®. In addition, a microchannel may also be used as the carrier. Here, the microchannel refers to a microchip or the like in which high-precision channels of the micron order are formed on a flow channel cell or a glass substrate; a protein may be immobilized on glass in the channels.

Here, examples of the commercially available immobilized carrier having functional groups introduced include Amino-Cellufine (sold by Seikagaku Corporation), AF-AminoTOYOPEARL (sold by TOSOH), EAH-Sepharose 4B and Lysine-Sepharose 4B (sold by Amersham Bioscience), Porus 20NH (sold by Boeringer Mannheim), POROS (sold by Life Technologies), CNBr-activated Sepharose FF, and NHS-activated Sepharose FF. One of ordinary skill in the art can easily introduce a functional group such as an amino group into a silica carrier, a glass bead, a flat plate of glass, or the like by using a silane compound having a primary amino group (for example, 3-aminopropylmethoxysilane).

When used in affinity chromatography for antibody purification, the carrier containing a Protein A mutant according to the present invention is used by filling a chromatography column with the carrier in particulate form.

The Protein A mutant having characteristics of strongly binding to the above antibody under neutral conditions and dissociating with the antibody bound under neutral conditions under weakly acidic conditions of pH 4.0 to 5.5 can be obtained by the following method.

Proteins are first prepared in each of which one amino acid is substituted by another amino acid in Protein A modified not to contain lysine or cysteine (e.g., the A-domain of Protein A, consisting of an amino acid shown in SEQ ID NO: 3). Among from these proteins, a Protein A mutant is selected which has characteristics of strongly binding to an antibody under neutral conditions and dissociating with the antibody bound under neutral conditions under weakly acidic conditions of pH 4.0 to 5.5. If necessary, proteins in each of which one amino acid is further substituted by another amino acid in the selected Protein A mutant, i.e., mutants having a plurality of amino acid substitutions combined, are prepared, and, among the mutants, a Protein A mutant is selected which has characteristics of strongly binding to an antibody under neutral conditions and dissociating with the antibody bound under neutral conditions under weakly acidic conditions of pH 4.0 to 5.5. This operation can be repeated several times to produce a Protein A mutant strongly offering the above characteristics. Finally, a Protein A mutant having a plurality of amino acids substituted can be obtained as a Protein A mutant having characteristics of strongly binding to an antibody under neutral conditions and dissociating with the antibody bound under neutral conditions under weakly acidic conditions of pH 4.0 to 5.5. For example, when the A-domain of Protein A is used as Protein A, a Protein A mutant can be obtained in which, in a mutant in which lysine and cysteine are substituted by other amino acids not to contain lysine and cysteine residues, 1, 2, or 3 amino acids are further substituted. In this case, 6 to 9 amino acids are substituted from wild-type amino acids including lysine and cysteine. A mutant can also be obtained in which, in a mutant in which lysine and cysteine are substituted by other amino acids not to contain lysine and cysteine residues in the whole Protein A, 1 to 9 amino acids are further substituted. In this case, 7 to 15 amino acids are substituted from wild-type amino acids including lysine and cysteine. Of these amino acids, 6 lysine and cysteine residues are substituted by other amino acids, and the remaining 1 to 9 amino acids are substituted to impart characteristics of strongly binding to an antibody under neutral conditions and dissociating with the antibody bound under neutral conditions under weakly acidic conditions of pH 4.0 to 5.5. Specific examples thereof include a mutant consisting of an amino acid sequence represented by the R2 part of each of the amino acid sequences of AD-3, AD-4, AD-6-1, and AD-6-2.

The characteristics of a Protein A mutant strongly binding to an antibody under neutral conditions and dissociating with the antibody bound under neutral conditions under weakly acidic conditions of pH 4.0 to 5.5 can be tested, for example, by the following method.

A protein is produced in which the amino acid sequence of a Protein A mutant is contained as the R2 part in an immobilized protein consisting of an amino acid sequence represented by the general formula: R1-R2-R3-R4-R5-R6, and the protein is used to immobilize the R1-R2-R3 part on an array substrate by the above method using cyanation. The array used here may be an array as described in JP Patent No. 4528951, JP Patent Publication (Kokai) No. 2010-127856, JP Patent No. 4006523, or the like.

The array substrate on which the mutant is immobilized is placed in an array analysis apparatus and connected to a solution feeding system in the apparatus; the array is irradiated with ultraviolet light at 280 nm while automatically passing a solution for the following analysis therethrough; and the transmitted light is photographed with time with CCD to capture the image of the array into PC. An initialization buffer solution (150 mM sodium chloride, 50 mM sodium phosphate, pH 7.0), an antibody solution (a solution in which a human polyclonal antibody is diluted to 0.2 mg/ml with a running buffer solution), a buffer solution for washing (1 M sodium chloride, 50 mM sodium phosphate, pH 7.0), a buffer solution for elution (0.1 M sodium citrate, pH 5.0), and a buffer solution for regeneration (0.1 M glycine, pH 2.5) are passed therethrough at a speed of 0.6 ml/min for 25 minutes in that order, and the array image is photographed with time at 8-second intervals and captured into PC for saving. In data analysis, an analysis software provided with the apparatus is used to automatically detect a spot in the array image to calculate the average brightness of pixels in the spot region and the average brightness of pixels around the spot to determine the logarithm of the ratio therebetween as the signal intensity of the spot. This value is confirmed to be proportional to the amount of the protein on the spot. The signal intensity of each spot is plotted against time elapsed from the start of passage through the array substrate. The curve created from the plots of the signal intensity against the elapsed time can be analyzed to evaluate the characteristics of the mutant protein. The time course of the signal intensity can be determined to quantitatively analyze a state where the antibody adsorbs and dissociates. A decay curve is fitted to a change in signal intensity during the elution to determine elapsed time until the half amount of the bound antibody is dissociated ($T_{0.5}$) to calculate the ratio thereof to $T_{0.5}$ for the above A-domain of the Protein A in AD-1 adjacent the array to determine normalized $T_{0.5}$ to evaluate this value as an indication of acid elution characteristics or an indication of ease of acid elution. Lower $T_{0.5}$ can be determined as indicating better acid elution characteristics, i.e., better characteristics of dissociating with the antibody bound under neutral conditions under weakly acidic conditions of pH 4.0 to 5.5. In addition to $T_{0.5}$, the dissociation constant with the antibody (Kd) may also be used as an indication.

The dissociation constant can be measured, for example, by performing the binding characterization between a Protein A mutant and an antibody by using Biacore (Biacore Co., Ltd.) as a surface plasmon resonance biosensor. On this occasion, a protein in which the amino acid sequence of a Protein A mutant is contained as the R2 part in an immobilized protein consisting of an amino acid sequence represented by the general formula: R1-R2-R3-R4-R5-R6 may be used to bind the R1-R2-R3 part to a carrier to use the protein-immobilized carrier. A change in mass over time on the surface plasmon resonance sensor surface observed may be measured using RU (the unit defined by Biacore) to determine the binding rate constant (kass), dissociation rate constant (kdis), and dissociation constant (Kd=kass/kdis). A Protein A mutant having a smaller dissociation constant can be determined as being a mutant capable of more strongly binding to an antibody under neutral conditions.

Figure 1:
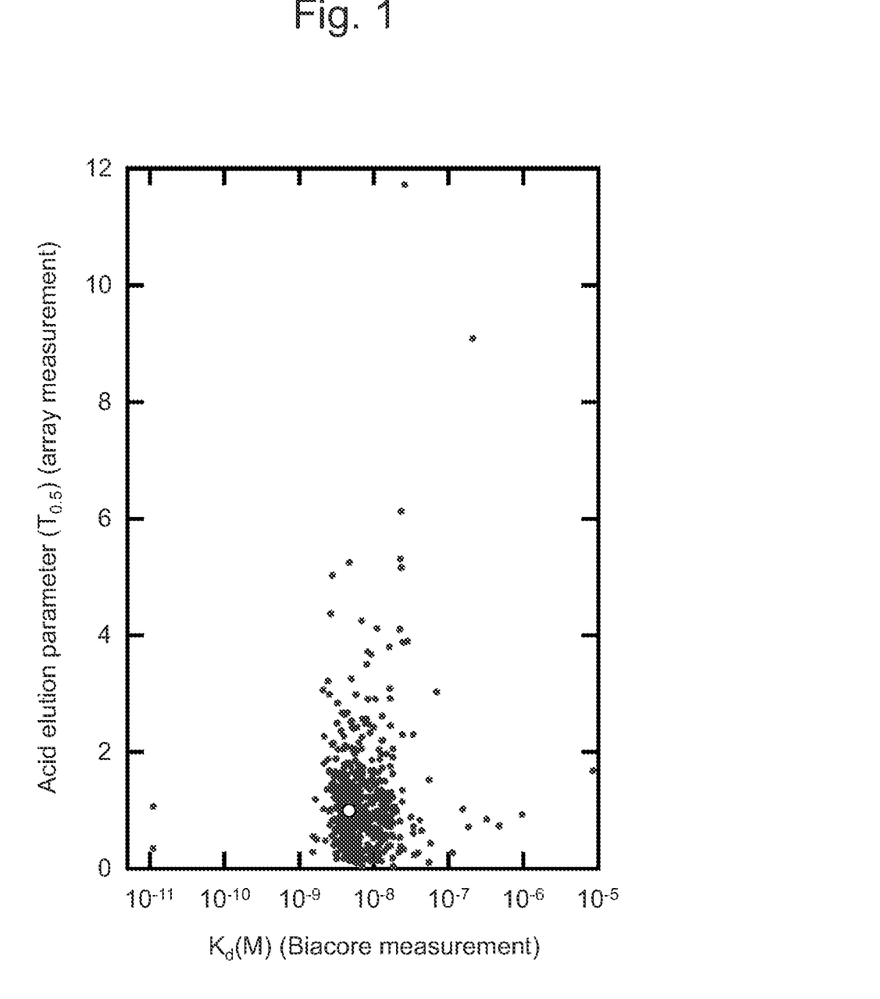
FIG. 1 is a graph showing the results of plotting the values of the elution parameter and $T_{0.5}$ of AD-1 at pH 5.0.

$T_{0.5}$ and the dissociation constant determined by the above method are plotted on a coordinate plane as shown in FIG. 1, and a mutant of the A-domain of Protein A, for which $T_{0.5}$ and the dissociation constant are in constant value ranges, i.e., are plotted in specific ranges on the coordinates, may be selected as a mutant excellent in characteristics of strongly binding to an antibody under neutral conditions and dissociating with the antibody bound under neutral conditions under weakly acidic conditions of pH 4.0 to 5.5.

For example, the same analysis is performed for a carrier on which the A-domain of Protein A is immobilized, prepared using AD-1 represented by the above-described SEQ ID NO: 2, and a Protein A in which $T_{0.5}$ is smaller than $T_{0.5}$ obtained by measurement using the A-domain of Protein A in AD-1 and the dissociation constant is smaller than the dissociation constant obtained by measurement using the A-domain of Protein A in AD-1 can be selected as a mutant excellent in characteristics of strongly binding to an antibody under neutral conditions and dissociating with the antibody bound under neutral conditions under weakly acidic conditions of pH 4.0 to 5.5 according to the present invention. The mutant excellent in characteristics of strongly binding to an antibody under neutral conditions and dissociating with the antibody bound under neutral conditions under weakly acidic conditions of pH 4.0 to 5.5 according to the present invention has a $T_{0.5}$ (when measured using the above array) of 1.00 or less, preferably 0.80 or less, more preferably 0.60 or less, particularly preferably 0.55 or less, and a dissociation constant (measured using the above-described Biacore) of $6\times10^{-9}$ or less, preferably $8\times10^{-9}$ or less, more preferably $10^{-10}$ or less.

The immobilization carrier on which a protein consisting of an amino acid sequence represented by the general formula: R1-R2-R3-R4-R5-R6 is immobilized according to the present invention can be used to provide an immobilized protein in which the part represented by R1-R2-R3 is immobilized. The immobilization carrier on which a protein consisting of an amino acid sequence represented by the general formula: R1-R2-R3-R4-R5-R6 is immobilized can be produced by adsorbing a protein consisting of an amino acid sequence represented by the general formula: R1-R2-R3-R4-R5-R6 on an immobilization carrier. The adsorption of the protein to the immobilization carrier may be performed by reacting the protein with the immobilization carrier under neutral to weakly alkaline conditions (pH 7 to 10) as described above. In an immobilization carrier on which a protein consisting of an amino acid sequence represented by the general formula: R1-R2-R3-R4-R5-R6 is immobilized, the cysteine residue contained in the R3 part of the protein can be cyanated to produce an immobilization carrier on which a protein consisting of an amino acid sequence represented by the general formula: R1-R2-R3 is immobilized, as described above. The present invention also encompasses the immobilization carrier on which a protein consisting of an amino acid sequence represented by R1-R2-R3 is immobilized.

An antibody can be purified by affinity chromatography using the immobilization carrier on which a protein consisting of an amino acid sequence represented by R1-R2-R3 is immobilized. The affinity chromatography column used for the affinity chromatography can be produced by filling a column with the immobilization carrier on which a protein consisting of an amino acid sequence represented by R1-R2-R3 is immobilized. The column can be filled with the carrier by a well-known method. The present invention also encompasses the affinity chromatography column for antibody purification containing an immobilization carrier on which a protein consisting of an amino acid sequence represented by R1-R2-R3 is immobilized.

The antibody purification using the affinity chromatography column of the present invention can be performed by a well-known affinity chromatography method; it is characterized in that the antibody bound to a Protein A mutant can be eluted from the antibody under mild pH conditions. In antibody purification, a solution containing the antibody to be purified (raw material crude solution) is first passed through an affinity chromatography column filled with an immobilization carrier on which a protein consisting of an amino acid sequence represented by R1-R2-R3 is immobilized to adsorb the antibody to a Protein A mutant on the carrier. On this occasion, the raw material crude solution is adjusted to pH 6.0 to 8.5 in advance. The buffer solution used for pH adjustment is not limited; however, for example, sodium phosphate, potassium phosphate, HEPES (2-[4-(2-hydroxyethyl)-1-piperazinyl]ethanesulfonic acid), or MES (2-morpholinoethanesulfonic acid) may be used. The affinity chromatography column is preferably equilibrated using the above buffer solution of pH 6.0 to 8.5 in advance. Then, the carrier to which the antibody is adsorbed is washed with a neutral buffer solution such as a sodium phosphate buffer solution or a Tris-HCl buffer solution to remove impurities. Thereafter, the bound antibody may be eluted using a buffer solution of pH 4.0 to 5.5 for recovery. The buffer solution of pH 4.0 to 5.5 may be a sodium acetate buffer solution, a sodium citrate buffer solution, a sodium phosphate buffer solution, MES (2-morpholinoethanesulfonic acid), or the like. The concentration of the buffer solution used is not limited; however, the solution may be used at a concentration of 10 to 50 mM. Depending on the volume of the antibody-containing raw material crude solution used as a sample, the column size may be, for example, 2.5 to 30 cm in length.

EXAMPLES

The present invention will be described below with reference to Examples. However, the present invention is not limited to these Examples.

In Examples below, the following experimental methods are commonly used.

Example 1

Gene Synthesis

Genes as described in Examples were synthesized by a contracted manufacturer of synthetic genes. dsDNA was synthesized based on the nucleotide sequence (SEQ ID NO: 8) shown below and inserted into the BamHI-EcoRI site of pUC18 vector; the sequences of the acquired clone were confirmed by single strand analysis and the cross-check of information of the nucleotide sequences was performed; mutation correction was performed by a method such as site directed mutagenesis for sites identified as being mismatched; and the resultant acquired plasmid DNA (about 1 μg) was delivered. A desired part of the delivered plasmid was again confirmed for the sequence thereof by sequencing.

Nucleotide Sequence of SEQ ID NO: 8

GGATCCTTGACAATATCTTAACTATCTGTTATAATATATTGACCAGGTTA

ACTAACTAAGCAGCAAAAGGAGGAACGACTATGGCGGATAACAACTTTAA

CCGCGAACAGCAGAACGCGTTTTATGAAATTCTGAACATGCCGAACCTGA

ACGAAGAACAGCGCAACGGCTTTATTCAGAGCCTGCGCGATGATCCGAGC

CAGAGCGCGAATCTGCTGAGCGAAGCGCGTCGTCTGAATGAAAGCCAGGC

GCCGGGCTGTGCGGATGACGACGACGATGATCACCACCATCACCATCATT

AAGAATTC

Preparation of Single Amino Acid Substitution Mutant

The amino acid substitution in the A-domain of Protein A based on AD-1 (whose amino acid sequence was shown in SEQ ID NO: 2) was performed by converting the DNA sequence encoding the amino acid of a site to be substituted to a desired codon sequence and following the QuickChang method (the method described in QuickChang Site-directed Mutagenesis kit from Stratagene Co., Ltd.) using a DNA primer and its complementary DNA primer each of which has the original sequence of 24 nucleotides.

Protein Purification

*Escherichia coli.* strain JM109 transformed with the recombinant plasmid was cultured at 35° C. overnight in 2 L of a medium (containing 20 g of sodium chloride, 20 g of yeast extract, 32 g of trypsin, and 100 mg of sodium ampicillin). Thereafter, the culture solution was subjected to low-speed centrifugation (at 5,000 rpm) for 20 minutes to provide 3 to 5 g by wet weight of bacterial cells. These bacterial cells were suspended in 20 mL of a 10 mM phosphate buffer solution (pH 7.0), and the cells were crushed using a French press apparatus, followed by high-speed centrifugation (at 20,000 rpm) for 20 minutes to separate the supernatant. Streptomycin sulfate was added to a final concentration of 2% to the resultant supernatant and stirred for 20 minutes, which was then subjected high-speed centrifugation (20,000 rpm) for 20 minutes to separate the supernatant. Then, the resultant was treated with ammonium sulfate; the supernatant was applied to a nickel chelate column (purchased from GE Healthcare Bioscience Corporation); the column was well washed with 20 ml or more of a buffer solution for washing (5 mM imidazole, 20 mM sodium phosphate, 0.5 M sodium chloride, pH 7.4); and after washing, 20 ml of a buffer solution for elution (0.5 M imidazole, 20 mM sodium phosphate, 0.5 M sodium chloride, pH 7.4) was applied to elute the desired protein. Thereafter, to remove imidazole from the protein solution, it was dialyzed against 5 L of a 10 mM phosphate buffer solution (pH 7.0). MWCO3500 (purchased from Spectrum Laboratories Co., Ltd.) was used as a dialysis membrane. After dialysis, the desired protein was dried using a centrifugal vacuum dryer.

Binding Characterization of Human IgG Antibody Molecule

The binding characterization of the desired protein was carried out using Biacore (Biacore Co., Ltd.) as a surface plasmon resonance biosensor according to the protocol provided by Biacore Co., Ltd.

As a running buffer solution, one having a composition of 10 mM HEPES (pH 7.4), 150 mM sodium chloride, 5 μM EDTA, and 0.005% Surfactant P20 (Biacore Co., Ltd.) and deaerated in advance was used.

SensorChip NTA (Biacore Co., Ltd.) was used as a sensor chip. The sensor chip was well equilibrated using the running buffer solution, followed by injecting a 5 mM nickel chloride solution to complete the coordination of nickel ions. Then, a recombinant protein solution (having a concentration of 100 μg/mL in the running buffer solution) was injected into the sensor chip to immobilize the recombinant protein.

For the binding reaction between the immobilized recombinant protein and human IgG, human IgG (Sigma-Aldrich, Inc.) solutions diluted/prepared to 7 concentrations of 0.25 to 20 μg/ml using the running buffer solution were sequentially injected, and subsequently replaced by the running buffer solution to maintain feeding to quantitatively observe the binding/dissociation phenomenon of the antibody. The feeding flow rate was set to 20 μL/min.; the time of observing binding (the antibody solution injection time), to 4 minutes; and the time of observing dissociation, to 4 minutes. The antibody solutions at the respective concentrations were each injected to observe the binding/dissociation phenomenon, followed by subsequently injecting a 6 M guanidine hydrochloride solution for 3 minutes to dissociate all human IgG bound to the immobilized recombinant protein, which was then regenerated with the running buffer solution and used for subsequent measurement.

The observed change in mass over time on the surface plasmon resonance sensor surface was measured using RU (the unit defined by Biacore) to determine the binding rate constant (kass), dissociation rate constant (kdis), and dissociation constant (Kd=kass/kdis).

The results of plotting dissociation constants indicating the strength of the binding of exhaustive single amino acid substitution mutants of the A-domain of Protein A in AD-1 to the antibody by Biacore measurement against the values of the elution parameter ($T_{0.5}$) determined from elution at pH 5.0 obtained by measurement using an array analysis apparatus are shown in FIG. 1.

Analysis of Acid Elution Characteristic of Antibody Using Array Analysis Apparatus The measurement using an array analysis apparatus was carried out as follows.

Immobilization of Protein on Array Substrate

Each mutant protein was dissolved in a 10 mM phosphate buffer solution of pH 7.0, which was adjusted to a final concentration of 2 mg/ml by measuring the concentration thereof by the BCA method. 0.2 μL each of about 2 mg/ml of the protein solutions were spotted at intervals of 1.2 mm at 96 points on a 8×12 matrix on an array substrate (a thin layer of silica monolith porous material). In this regard, the same mutant protein was spotted at 2 points on one array to ensure the confirmation of the reproducibility of data. AD-1 protein was spotted as a protein for comparison at 2 points on each line to ensure the comparison between data for each mutant protein and data for AD-1 protein. After spotting, a reduction reaction, a cyanation reaction, an orientation-controlled immobilization reaction via cyanocysteine, washing with a buffer solution having a high salt concentration, and a reaction masking the remaining amino groups were sequentially carried out for each protein to immobilize the protein on an array substrate.

Measurement

The array substrate on which the mutants were spot-immobilized was placed in an array analysis apparatus and connected to a solution feeding system in the apparatus; the array was irradiated with ultraviolet light at 280 nm while automatically passing a solution for analysis as described below therethrough; and the transmitted light was photographed with time with CCD to capture the image of the array into PC. An initialization buffer solution (150 mM sodium chloride, 50 mM sodium phosphate, pH 7.0), an antibody solution (a solution in which a human polyclonal antibody was diluted to 0.2 mg/ml with a running buffer solution), a buffer solution for washing (1 M sodium chloride, 50 mM sodium phosphate, pH 7.0), a buffer solution for elution (0.1 M sodium citrate, pH 5.0), and a buffer solution for regeneration (0.1 M glycine, pH 2.5) were passed therethrough at a speed of 0.6 ml/min. for 25 minutes in that order, and the array image was photographed with time at 8-second intervals and captured into PC for saving.

Data Analysis

In data analysis, an analysis software provided with the apparatus was used to automatically detect a spot in the array image to calculate the average brightness of pixels in the spot region and the average brightness of pixels around the spot to determine the logarithm of the ratio therebetween as the signal intensity of the spot. This value has been confirmed to be proportional to the amount of the protein on the spot. The signal intensity of each spot was plotted against time elapsed from the start of passage through the array substrate. The curve created from the plots of the signal intensity against the elapsed time was analyzed to evaluate the characteristics of the mutant protein. The time course of the signal intensity can be determined to quantitatively analyze a state where the antibody adsorbs and dissociates.

As a result of the analysis, it was found that the speed of dissociation of the antibody when the buffer solution for elution was passed, i.e., the acid elution characteristics of the antibody, greatly varied depending on the type of the mutant protein. Accordingly, a decay curve was fitted to a change in signal intensity during the elution to determine the elapsed time until the half amount of the adsorbed antibody was dissociated ($T_{0.5}$) to calculate the ratio thereof to $T_{0.5}$ for the above A-domain of the Protein A in AD-1 adjacent the array to determine normalized $T_{0.5}$ to use this value as an indication of acid elution characteristics or an indication of ease of acid elution.

Then, the selection of mutant proteins was attempted based on the indications of both of the acid elution characteristics and the dissociation constant (Kd) determined by the method described in the above-described "Binding Characterization of Human IgG Antibody Molecule" as indications. As a result, a plurality of mutant proteins could be selected which had high binding affinity (low values of Kd) and were easily subjected to acid elution (had low values of $T_{0.5}$) compared to for the A-domain of Protein A in AD-1. A mutant protein more easily subjected to acid elution could be found by preparing mutant proteins in each of which the mutations were combined and preparing an array therefor to measure/analyze the acid elution characteristics of the antibody.

The amino acid sequence shown in SEQ ID NO: 1 in which E (glutamic acid) at position 15 was substituted by H (histidine) (E15H) had good acid elution characteristics.

Example 2

Based on the results of Example 1, other single amino acid substitution mutations were further added to the E15H mutation. As added mutations, substitution mutations at the sites of M19 (methionine at position 19 in the amino acid sequence shown in SEQ ID NO: 1) and G29 (glycine at position 29 in the amino acid sequence shown in SEQ ID NO: 1) were examined. This is because M19 is a methionine residue solely present in AD-1 and sensitive to air oxidation and the amino acid substitution of this site is expected to add antioxidative performance as a chemical property. The site of G29 is a site shown as one of sites whose mutation is expected to improve elution characteristics at pH 5.0 as a result of array analysis. For the site of M19, M19V (substitution of V (valine) for methionine at position 19) was selected as a mutation in which is improved $T_{0.5}$ as a parameter of ease of elution at pH 5, and for the site of G29, G29A (substitution of A (alanine) for glycine at position 29), G29D (substitution of D (aspartic acid) for glycine at position 29), and G29E (substitution of E (glutamic acid) for G at position 29) were selected. The results are shown in Table 1.

TABLE 1

| Residue No. | Name | Kd (hIgG) | Kon | Koff | $T_{0.5}$ (pH 5.0) |
|---|---|---|---|---|---|
| 15 | E15H | 1.11E−11 | 6.05E+04 | 6.70E−07 | 0.46 |
| 19 | M19V | 1.17E−08 | 4.69E+04 | 5.50E−04 | 0.53 |
| 29 | G29A | 2.92E−09 | 2.44E+05 | 7.12E−04 | 0.49 |
|  | G29D | 4.49E−09 | 1.12E+05 | 5.03E−04 | 0.38 |
|  | G29E | 2.87E−09 | 2.10E+05 | 6.03E−04 | 0.40 |

Preparation of expression genes, expression in *Escherichia coli*, and separation and purification of expressed recombinant proteins from *Escherichia coli* were carried out according to the above methods for the 4 combination mutations of E15H+G29A (the R2 part in AD-3), E15H+M19+G29A (the R2 part in AD-4), E15H+M19+G29D (the R2 part in AD-6-2), and E15H+M19+G29E (the R2 part in AD-6-1) as combination mutations in each of which the above mutations were combined to prepare about 1 g each of purified products of the respective proteins. Using each prepared protein, a protein represented by the general formula: R1-R2-R3-R4-R5-R6 was prepared. The R2 part was each of the above mutants of Protein A; R1 is absent; R3 is the sequence represented by Gly-Gly-Gly-Gly; R4 is the sequence represented by Cys-Ala; R5 is the sequence represented by Asp-Asp-Asp-Asp-Asp-Asp; and R6 is the sequence represented by His-His-His-His-His-His. According to methods as described in JP Patent No. 3788828 or 2990271 or JP Patent Publication (Kokai) No. 2003-344396 A, 2008-115151 A, 2008-115152 A, 2008-115153 A, or 2008-266221 A, and the like, cysteine in the R4 part was cyanated to make cyanocycteine, and the R1-R2-R3 part (actually, the R2-R3 part) was immobilized on a carrier to prepare each affinity carrier into which a ligand was introduced. The preparation method therefor is shown in the following "Immobilization of Recombinant Protein". The above "affinity carrier into which a ligand was introduced" is the same as the following "protein-immobilized silica gel". A separation column using about 1 ml of each affinity carrier was prepared. Chromatography using a polyclonal antibody was carried out with each prepared separation column, and pH during elution was changed to measure the pH dependence of the elution/recovery amount of the antibody.

The chromatography using an immobilization carrier was carried out by a method as described below.

Akta from GE Healthcare Co., Ltd. was used as a liquid chromatography apparatus.

A column (1 ml) (size: 4: ɸ=5 mm, height=50 mm) was filled with the carrier on which a ligand was immobilized (protein-immobilized silica gel), and attached to the liquid chromatography apparatus.

First, (1) (initialization) 10 ml of 10 mM sodium phosphate buffer was passed;

(2) (sample application) then, by using a sample loop, a polyclonal IgG antibody solution (1 ml) was passed and a solvent-switching valve was switched;

(3) (washing) 10 ml of 10 mM sodium phosphate buffer was passed, and then a solvent-switching valve was switched;

(4) (elution) 10 ml of a citrate buffer solution having each pH set in advance was passed, and a solvent-switching valve was switched;

(5) (regeneration) 10 ml of a solution for regeneration (a 0.1 M citric acid solution) was passed, and a solvent-switching valve was switched; and (6) (completion) 10 ml of 10 mM sodium phosphate buffer in (1) was passed to complete the operation of passage in the chromatography.

During passage, the solution eluted from the column was measured for absorbance at 280 nm and electric conductivity by using a UV detector and an electric conductivity meter included in the apparatus, and the resultant values were recorded. From a chromatogram curve using absorbance at 280 nm, the elution peak was identified and its peak area was calculated; and it was determined by calculation how the applied antibody was recovered.

Figure 2:
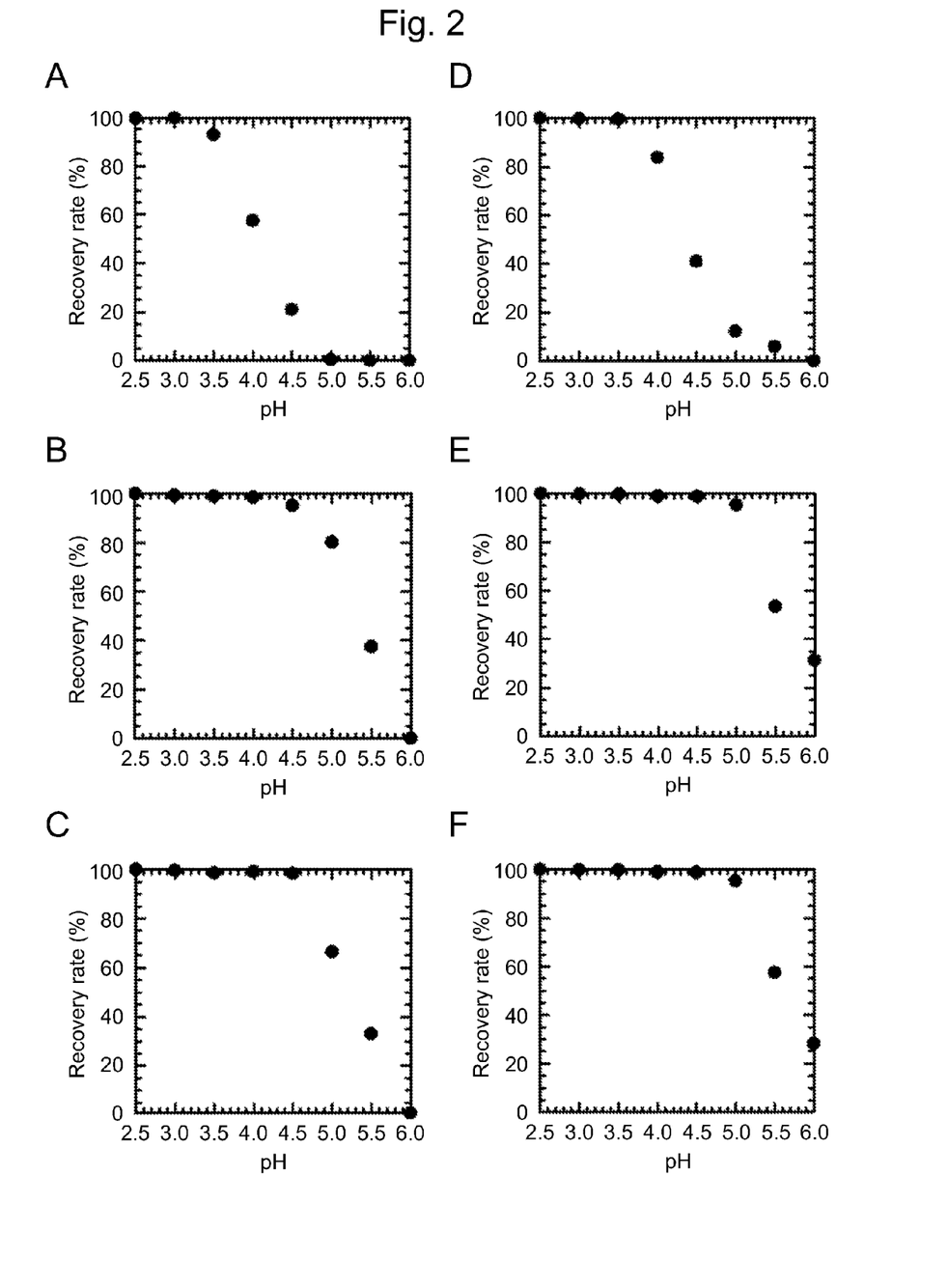
FIG. 2 is a series of graphs showing the pH dependence of the amount of elution/recovery of an antibody in affinity chromatography using each Protein A. In the graphs of A to F of FIG. 2, the horizontal axis represents the pH of the buffer solution used for elution, and the vertical axis represents the recovery rate (%) (black circle) of the antibody eluted when elution was performed at each pH.

The results are shown in FIG. 2. A of FIG. 2 shows the results for the R2 part in AD-2; B, for the R2 part in AD-3; C, for the R2 part in AD-4; D, for the R2 part in AD-5; E, for the R2 part in AD-6-1; and F, for the R2 part in AD-6-2.

Figure 3:
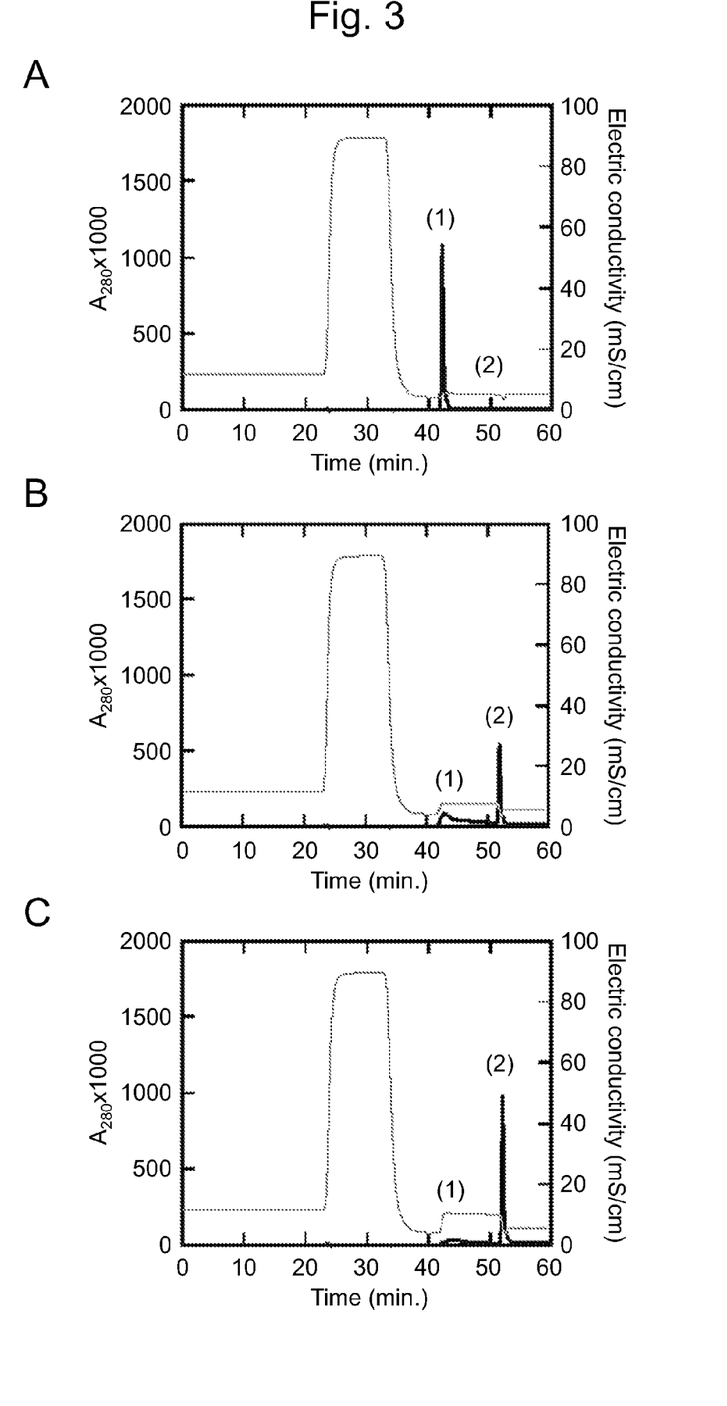
FIG. 3 is a series of graphs showing the chromatograms of affinity chromatography using a Protein A. The graphs of A, B, and C of FIG. 3 show chromatograms when using eluting solutions having pHs of 3.0, 4.0, and 5.0, respectively.

The chromatograms of affinity chromatography using an immobilization carrier are shown in FIG. 3.

A, B, and C of FIG. 3 show chromatograms at pHs 3.0, 4.0, and 4.5, respectively. In FIG. 3, (1) shows an elution peak when the elution solution at pH 3.0, 4.0, or 4.5 was flowed, and (2) shows an elution peak when the solution for regeneration (pH 2.5) was flowed. The areas of the (1) and (2) elution peaks (referred to as S1 and S2, respectively) are used to calculate the recovery rates by 100*S1/(s1+S2), and FIG. 2 is a series of graphs in each of which the resultant values are plotted against the pHs of the elution solution.

Immobilization of Recombinant Protein 50 g of Silica Gel (from Daiso Co., Ltd.) was reacted with 10 g of 3-glycidoxypropyltrimethoxysilane in an aqueous medium under reflux conditions (95° C.) for 4 hours to prepare 50 g of epoxidized silica gel.

Epoxidized silica gel obtained as described above was suspended in 0.1 M borate buffer (pH 9.5), to which 5 g of poly-L-lysine (P6516 from Sigma) was then added, followed by stirring at room temperature for 24 hours. Then, 500 ml of a 5 mM 2-nitro-5-thiocyanobenzoate solution and 2 g of a recombinant protein (AD-3, AD-4, AD-6-1, or AD-6-2) were added thereto and stirred for 24 hours, and the buffer was subsequently replaced by 10 mM borate buffer (pH 9.5), followed by again stirring for 24 hours to finally prepare 47 g of silica gel on which each recombinant protein was immobilized.

Measurement of IgG Binding Capacity of Immobilization Carrier

The IgG binding capacity of the immobilization silica gel prepared above was measured as follows.

A glass column (5 mm ɸ×20 mm) (0.4 ml, from GE Healthcare Co., Ltd.) was filled with a carrier on which the A-domain of Protein A in AD-3 was immobilized. A known concentration of human polyclonal IgG antibody dissolved in pH7 sodium phosphate buffer (0.5 mg/ml, from Oriental Yeast Co., Ltd.) was loaded under various contact times (1.0, 2.4, and 6.0 min.). From a breakthrough curve here was calculated the 10% breakthrough point, from which the following dynamic binding capacity (DBC) was obtained for each contact time. From the table, the static binding capacity could be estimated to be about 60 mg/ml. The results are shown in Table 2.

TABLE 2

| | Contact Time (min) | | |
|---|---|---|---|
| | 1.0 | 2.4 | 6.0 |
| 10% Dynamic Binding Capacity (mg/ml) | 45 | 62 | 62 |

In like manner, the binding capacity was measured for the A-domain of Protein A in each protein of AD-4, AD-6-1, and AD-6-2, and the following results were obtained. The results are shown in Table 3.

TABLE 3

| | | Contact Time | | |
|---|---|---|---|---|
| | | 1.0 | 2.4 | 6.0 |
| 10% Dynamic Binding Capacity (mg/ml) | AD-4 | 43 | 60 | 60 |
| | AD-6-1 | 45 | 61 | 63 |
| | AD-6-2 | 44 | 59 | 60 |

INDUSTRIAL APPLICABILITY

The technical filed to which this invention relates includes a wide range of technical fields in which immobilized antibodies are involved, for example, the fields of testing techniques, such as component testing and clinical testing, using antibody columns and antibody arrays as well as immobilized antibodies, and the fields of separation and purification using antibody columns.

SEQUENCE LISTING FREE TEXT

SEQ ID NOS: 1 to 8 Synthesis

All publications, patents, and patent applications cited in this application are intended to be incorporated herein by reference in their entirety.

The invention claimed is:

1. An immobilization carrier, excluding an immobilization carrier having a monolith structure, onto which a protein is adsorbed by electrostatic interaction, the protein consisting of an amino acid sequence of the general formula: R1-R2-R3-R4-R5-R6, wherein R1-R2-R3 is used for immobilization on the immobilization carrier, wherein:
the amino acid sequence is a sequence from the amino-terminal side towards the carboxyl-terminal side;
R1 may be absent, and, if present, is Met;
R2 is the sequence of a mutant protein of the A-domain of Protein A consisting of a sequence selected from SEQ ID NOS: 4 to 7, or a sequence wherein 1 to 3 units of the sequence of the mutant protein of the A-domain of the Protein A consisting of a sequence selected from SEQ ID NO: 4 to 7 are linked together;
R3 may be absent, and, if present, is a spacer sequence consisting of 1 to 10 glycine residues;
R4 is a sequence consisting of 2 residues of amino acids: cysteine-X, wherein X is alanine or an amino acid residue other than alanine and cysteine;
R5 may be absent, and, if present, is a sequence of 1 to 10 amino acid residues consisting of aspartic acid, glutamic acid, or a combination thereof capable of rendering the isoelectric point of the protein consisting of the amino acid sequence of the general formula: R1-R2-R3-R4-R5-R6 on the acidic side; and
R6 is an affinity tag sequence for the purification of proteins.

2. The immobilization carrier of claim 1, for converting the sulfhydryl group of the sole cysteine residue present in the protein consisting of the amino acid sequence of the general formula: R1-R2-R3-R4-R5-R6 to a thiocyano group and causing a resultant to act on any immobilization carrier having a primary amine as a functional group for binding the R1-R2-R3 part which is the amino acid sequence part present at the amino-terminal side to the cysteine residue of the protein to the carrier by amide bonding.

3. The immobilization carrier of claim 1, wherein R5 is an amino acid sequence consisting of 1 to 10 aspartic acid residues.

4. The immobilization carrier of claim 1, wherein R6 is an amino acid sequence consisting of 4 to 7 histidine residues.

5. The immobilization carrier according to claim 1, wherein the carrier is selected from the group consisting of silica carriers, glass beads, and polymers.

6. A method for preparing the immobilization carrier of claim 1, comprising adsorbing the protein consisting of an amino acid sequence of the general formula: R1-R2-R3-R4-R5-R6 onto a carrier by electrostatic interaction.

7. An immobilization carrier onto which a Protein A mutant is immobilized, produced by converting the sulfhydryl group of the sole cysteine residue present in the protein consisting of an amino acid sequence of the general formula: R1-R2-R3-R4-R5-R6 of claim 1 to a thiocyano group and causing a resultant to act on any immobilization carrier having a primary amine as a functional group for binding the R1-R2-R3 part as an amino acid sequence part present at the amino-terminal side to the cysteine residue of the protein to the carrier by amide bonding.

8. A method for preparing the immobilization carrier of claim 6, comprising converting the sulfhydryl group of the sole cysteine residue present in the protein consisting of an amino acid sequence of the general formula: R1-R2-R3-R4-R5-R6 to a thiocyano group and causing a resultant to act on any immobilization carrier having a primary amine as a functional group for binding the R1-R2-R3 part as an amino acid sequence part present at the amino-terminal side to the cysteine residue of the protein to the carrier by amide bonding.

9. An affinity chromatography column for antibody purification, filled with the immobilization carrier according to claim 7.

10. A method for purifying an antibody, comprising applying a solution comprising an antibody to the affinity chromatography column for antibody purification according to claim 9 to bind the antibody to the Protein A mutant and then dissociating and eluting the antibody using an elution buffer solution.

11. A method for designing a protein consisting of an amino acid sequence of the general formula: R1-R2-R3-R4-R5-R6 used for immobilization of a protein consisting of an amino acid sequence of R1-R2-R3 on an immobilization carrier, comprising selecting the amino acid sequences of the R1, R2, R3, R4, R5, and R6 parts so as to conform to the following conditions:

(a) permitting the sequence of the R1 part to be absent, or, if permitting the presence thereof, selecting a sequence consisting of Met;
(b) as the sequence of the R2 part, selecting the sequence of a mutant protein of the A-domain of a Protein A mutant consisting of an amino acid sequence selected from SEQ ID NOS: 4 to 7 or a sequence wherein 1 to 3 units of the sequence of a mutant protein of the A-domain of a Protein A consisting of an amino acid sequence selected from SEQ ID NO: 4 to 7 are linked together;
(c) permitting the sequence of the R3 part to be absent, or, if permitting the presence thereof, selecting a spacer sequence consisting of 1 to 10 glycine residues;
(d) as the sequence of the R4 part, selecting a sequence composed of 2 residues of amino acids: cysteine-X, wherein X represents alanine or an amino acid residue other than cysteine;
(e) of 1 to 10 amino acid residues consisting of amino acid residues of aspartic acid and/or glutamic acid capable of rendering the isoelectric point of the whole protein consisting of an amino acid sequence of the general formula: R1-R2-R3-R4-R5-R6 on the acidic side; permitting the sequence of the R5 part to be absent, or, if permitting the presence thereof, selecting a sequence and
(f) as the sequence of the R6 part, selecting an affinity tag sequence for purifying a protein.

12. The immobilization carrier of claim 1, wherein R4 is Cys-Ala.

13. The method of claim 11, wherein R5 is an amino acid sequence consisting of 1 to 10 aspartic acid residues.

14. The method of claim 11, wherein R6 is an amino acid sequence consisting of 4 to 7 histidine residues.

15. The method of claim 11, wherein R4 is Cys-Ala.

16. The immobilization carrier of claim 1, consisting of an amino acid sequence of SEQ ID NO: 2.

* * * * *

```
                       SEQUENCE LISTING

<160> NUMBER OF SEQ ID NOS: 8

<210> SEQ ID NO 1
<211> LENGTH: 58
<212> TYPE: PRT
<213> ORGANISM: Artificial
<220> FEATURE:
<223> OTHER INFORMATION: Synthetic

<400> SEQUENCE: 1

Ala Asp Asn Asn Phe Asn Lys Glu Gln Gln Asn Ala Phe Tyr Glu Ile
1               5                   10                  15

Leu Asn Met Pro Asn Leu Asn Glu Glu Gln Arg Asn Gly Phe Ile Gln
            20                  25                  30

Ser Leu Lys Asp Asp Pro Ser Gln Ser Ala Asn Leu Leu Ser Glu Ala
        35                  40                  45

Lys Lys Leu Asn Glu Ser Gln Ala Pro Lys
    50                  55

<210> SEQ ID NO 2
<211> LENGTH: 76
<212> TYPE: PRT
<213> ORGANISM: Artificial
<220> FEATURE:
<223> OTHER INFORMATION: Synthetic

<400> SEQUENCE: 2

Ala Asp Asn Asn Phe Asn Arg Glu Gln Gln Asn Ala Phe Tyr Glu Ile
1               5                   10                  15

Leu Asn Met Pro Asn Leu Asn Glu Glu Gln Arg Asn Gly Phe Ile Gln
            20                  25                  30

Ser Leu Arg Asp Asp Pro Ser Gln Ser Ala Asn Leu Leu Ser Glu Ala
        35                  40                  45

Arg Arg Leu Asn Glu Ser Gln Ala Pro Gly Gly Gly Gly Gly Cys Ala
    50                  55                  60

Asp Asp Asp Asp Asp His His His His His His
65                  70                  75

<210> SEQ ID NO 3
<211> LENGTH: 58
<212> TYPE: PRT
```

<213> ORGANISM: Artificial
<220> FEATURE:
<223> OTHER INFORMATION: Synthetic

<400> SEQUENCE: 3

Ala Asp Asn Asn Phe Asn Arg Glu Gln Gln Asn Ala Phe Tyr Glu Ile
1               5                   10                  15

Leu Asn Met Pro Asn Leu Asn Glu Glu Gln Arg Asn Gly Phe Ile Gln
            20                  25                  30

Ser Leu Arg Asp Asp Pro Ser Gln Ser Ala Asn Leu Leu Ser Glu Ala
        35                  40                  45

Arg Arg Leu Asn Glu Ser Gln Ala Pro Gly
    50                  55

<210> SEQ ID NO 4
<211> LENGTH: 58
<212> TYPE: PRT
<213> ORGANISM: Artificial
<220> FEATURE:
<223> OTHER INFORMATION: Synthetic

<400> SEQUENCE: 4

Ala Asp Asn Asn Phe Asn Arg Glu Gln Gln Asn Ala Phe Tyr His Ile
1               5                   10                  15

Leu Asn Met Pro Asn Leu Asn Glu Glu Gln Arg Asn Ala Phe Ile Gln
            20                  25                  30

Ser Leu Arg Asp Asp Pro Ser Gln Ser Ala Asn Leu Leu Ser Glu Ala
        35                  40                  45

Arg Arg Leu Asn Glu Ser Gln Ala Pro Gly
    50                  55

<210> SEQ ID NO 5
<211> LENGTH: 58
<212> TYPE: PRT
<213> ORGANISM: Artificial
<220> FEATURE:
<223> OTHER INFORMATION: Synthetic

<400> SEQUENCE: 5

Ala Asp Asn Asn Phe Asn Arg Glu Gln Gln Asn Ala Phe Tyr His Ile
1               5                   10                  15

Leu Asn Val Pro Asn Leu Asn Glu Glu Gln Arg Asn Ala Phe Ile Gln
            20                  25                  30

Ser Leu Arg Asp Asp Pro Ser Gln Ser Ala Asn Leu Leu Ser Glu Ala
        35                  40                  45

Arg Arg Leu Asn Glu Ser Gln Ala Pro Gly
    50                  55

<210> SEQ ID NO 6
<211> LENGTH: 58
<212> TYPE: PRT
<213> ORGANISM: Artificial
<220> FEATURE:
<223> OTHER INFORMATION: Synthetic

<400> SEQUENCE: 6

Ala Asp Asn Asn Phe Asn Arg Glu Gln Gln Asn Ala Phe Tyr His Ile
1               5                   10                  15

Leu Asn Val Pro Asn Leu Asn Glu Glu Gln Arg Asn Glu Phe Ile Gln
            20                  25                  30

Ser Leu Arg Asp Asp Pro Ser Gln Ser Ala Asn Leu Leu Ser Glu Ala

```
<210> SEQ ID NO 7
<211> LENGTH: 58
<212> TYPE: PRT
<213> ORGANISM: Artificial
<220> FEATURE:
<223> OTHER INFORMATION: Synthetic

<400> SEQUENCE: 7

Ala Asp Asn Asn Phe Asn Arg Glu Gln Gln Asn Ala Phe Tyr His Ile
1               5                   10                  15

Leu Asn Val Pro Asn Leu Asn Glu Glu Gln Arg Asn Asp Phe Ile Gln
            20                  25                  30

Ser Leu Arg Asp Asp Pro Ser Gln Ser Ala Asn Leu Leu Ser Glu Ala
        35                  40                  45

Arg Arg Leu Asn Glu Ser Gln Ala Pro Gly
    50                  55

<210> SEQ ID NO 8
<211> LENGTH: 308
<212> TYPE: DNA
<213> ORGANISM: Artificial
<220> FEATURE:
<223> OTHER INFORMATION: Synthetic

<400> SEQUENCE: 8
ggatccttga caatatctta actatctgtt ataatatatt gaccaggtta actaactaag      60
cagcaaaagg aggaacgact atggcggata caactttaa ccgcgaacag cagaacgcgt     120
tttatgaaat tctgaacatg ccgaacctga acgaagaaca gcgcaacggc tttattcaga    180
gcctgcgcga tgatccgagc cagagcgcga atctgctgag cgaagcgcgt cgtctgaatg    240
aaagccaggc gccgggctgt gcggatgacg acgacgatga tcaccaccat caccatcatt    300
aagaattc                                                             308
```

UNITED STATES PATENT AND TRADEMARK OFFICE
CERTIFICATE OF CORRECTION

PATENT NO. : 9,534,060 B2  
APPLICATION NO. : 14/406728  
DATED : January 3, 2017  
INVENTOR(S) : Masahiro Iwakura et al.

It is certified that error appears in the above-identified patent and that said Letters Patent is hereby corrected as shown below:

In the Claims

In Column 32, Claim 11, Line 19, before "1 to 10 amino" insert --permitting the sequence of the R5 part to be absent, or, if permitting the presence thereof, selecting a sequence--.

In Column 32, Claim 11, Lines 23-26, replace "acidic side; permitting the sequence of the R5 part to be absent, or, if permitting the presence thereof, selecting a sequence and" with --acidic side; and--.

Signed and Sealed this  
Twenty-fifth Day of July, 2017

Joseph Matal  
*Performing the Functions and Duties of the*  
*Under Secretary of Commerce for Intellectual Property and*  
*Director of the United States Patent and Trademark Office*